US006696425B2

(12) United States Patent
Yerxa et al.

(10) Patent No.: US 6,696,425 B2
(45) Date of Patent: *Feb. 24, 2004

(54) METHOD OF TREATING DRY EYE DISEASE WITH PURINERGIC RECEPTOR AGONISTS

(75) Inventors: Benjamin R. Yerxa, Raleigh, NC (US); Karla Jacobus, Cary, NC (US); William Pendergast, Durham, NC (US); Janet L. Rideout, Chapel Hill, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/027,520

(22) Filed: Dec. 19, 2001

(65) Prior Publication Data

US 2002/0193340 A1 Dec. 19, 2002

Related U.S. Application Data

(63) Continuation-in-part of application No. 10/010,055, filed on Nov. 9, 2001, which is a continuation of application No. 09/171,169, filed as application No. PCT/US98/08701 on Feb. 6, 1998, and a continuation-in-part of application No. 08/797,472, filed on Feb. 6, 1997, now Pat. No. 5,900,407.

(51) Int. Cl.$^7$ .............................................. A61K 31/70
(52) U.S. Cl. ............................ 514/47; 514/51; 514/912
(58) Field of Search ............................ 514/47, 51, 912

(56) References Cited

U.S. PATENT DOCUMENTS

| | | | |
|---|---|---|---|
| 4,380,239 A | | 4/1983 | Crawford et al. |
| 4,658,816 A | | 4/1987 | Ector, Jr. |
| 4,753,945 A | * | 6/1988 | Gilbard et al. ......... 514/263.31 |
| 4,868,154 A | * | 9/1989 | Gilbard et al. ................ 514/13 |
| 4,921,485 A | | 5/1990 | Griffiths |
| 5,021,043 A | | 6/1991 | Becker et al. |
| 5,062,831 A | | 11/1991 | Griffiths |
| 5,169,386 A | | 12/1992 | Becker et al. |
| 5,292,498 A | * | 3/1994 | Boucher, Jr. ................. 424/45 |
| 5,345,948 A | | 9/1994 | O'Donnell, et al. |
| 5,900,407 A | * | 5/1999 | Yerxa et al. .................... 514/47 |

FOREIGN PATENT DOCUMENTS

| WO | WO 97 35591 | 10/1997 |
|---|---|---|
| WO | WO 98 03177 A | 1/1998 |
| WO | WO 98 03182 A3 | 1/1998 |
| WO | WO 98 03182 A2 | 1/1998 |

OTHER PUBLICATIONS

Al–Hussein, H., et al., "Silastic Intubation in Congenital Nasolacrimal Duct Obstruction: A Study of 129 Eyes" *Ophthalmic Plastic & Reconstructive Surgery* 9(1):32–37 (1993).
Baker, J.C., et al., *Mutation Res.*, 208, 87 (1988).
Bartley, G.B., "Acquired Lacrimal Drainage Obstruction: An Etiologic Classification System, Case Reports, and a Review of the Literature. Part 1" *Ophthalmic Plastic Reconstructive Surgery*, 8(4):237–242 (1992).
Blackburn, G.M., et al., *Nucleosides & Nucleotides*, 10, 549 (1991).
Blicker, J.A., et al., "Lacrimal Sac, Conjunctival, and Nasal Culture Results in Dacryocystorhinostomy Patients," *Ophthalmic Plastic & Reconstructive Surgery*, 9(1):43–46 (1993).
Bone, R., et al., *J. Biol. Chem.*, 261, 16410 (1986).
Brown, H., et al., *Mol. Pharmocol.* 40, 648–55 (1991).
Burton, D., et al., *J. Fluorine Chem.* 15, 263–266 (1980.
Casillas, T., et al., *Biochemstry*, 32, 14203 (1993).
Castro, E., et al., *Br. J. Pharmacol.*, 100, 360 (1990).
Castro, E., et al., *Br. J. Pharmacol.*, 100, 360 (1990).
Castro, E., et al., *Br. J. Pharmacol.*, 106, 833 (1992).
Castro, E., et al., *J. Biol. Chem.*, 270, 5098 (1995).
Castro, E., et al., *Pflugers Arch.*, 426, 524 (1994).
Conway, S.T., "Evaluation and Management of "Functional" Nasolacrimal Blockage: Results of a Survey of the American Society of Ophthalmic Plastic and Reconstructive Surgey," *Ophthalmic Plastic & Reconstructive Surgey*, 10(3):185–188 (1994).
Coste, H., et al., *J. Biol. Chem.*, 262, 12096 (1987).
Dartt, D.A., et al., "Vasoactive Intestinal Peptide–Stimulated Glycoconjugate Secretion from Conjunctival Goblet Cells," *Exp. Eye. Res.*, 63:27–34 (1996).
Dortzbach, R.K., et al., "Silicone Intubation for Obstruction of the Nasolacrimal Duct in Children," *American Journal of Ophthalmology*. 94(5):585–590 (1982).
Drutz, D., et al., *Drug Dev. Res.* 37(3), 185 (1996).
Elmaleh, D.R., et al., *Proc. Natl. Acad. Sci.*, 81, 918 (1984).
Foster, J.A., et al., "Results of Dacryoscintigraphy in Massage of the Congenitally Blocked Nasolacrimal Duct," *Ophthalmic Plactic and Reconstructive Surgery* 12(1):32–37 (1996).

(List continued on next page.)

Primary Examiner—James O. Wilson
Assistant Examiner—Howard V. Owens, Jr.
(74) Attorney, Agent, or Firm—Albert P. Halluin; Viola T. Kung; Howrey, Simon, Arnold & White, LLP

(57) ABSTRACT

This invention is directed to a method of stimulating tear secretion and mucin production in eyes. The method comprises the step of administering to the eyes of a subject a composition comprising a compound of Formula I, II, III, or IV and its pharmaceutically acceptable salts, in an amount effective to stimulate tear fluid secretion. The method of the present invention may be used to increase tear production for any reason, including, but not limited to, treatment of dry eye disease and corneal injury. Pharmaceutical formulations and methods of making the same are also disclosed. Methods of administering the same would include: topical administration via a liquid, gel, cream, or as part of a contact lens or selective release membrane; or systemic administration via nasal drops or spray, inhalation by nebulizer or other device, oral form (liquid or pill), injectable, intra-operative instillation or suppository form.

18 Claims, 5 Drawing Sheets

OTHER PUBLICATIONS

Gilbard, J.P., "Dry Eye: Pharmacological Approaches, Effects, and Progress," *CLAO Journal* 22(2):141–145 (1996).

Gilbard, J.P., "Treatment of Keratoconjunctivitis Sicca in Rabbits With 3–Isobutyl–1–Methylxanthine," *Arch. Ophthalmol,.* 112:1614–1616 (1994).

Gilbard, J.P., et al., "Stimulation of Tear Secretion and Treatment of Dry–Eye Disease With 3–Isobutyl–1–methylxanthine," *Arch. Ophthalmol.* 109(5):672–676 (1991).

Gilbard, J.P., et al., "Stimulation of Tear Secretion by Topical Agents That Increase Cyclic Nucleotide Levels," *Investigative Ophthalmology & Visual Science,* 31(7):1381–1388 (1990).

Gilbard, J.P., et al., "Osomolarity of Tear Microvolumes in Keratoconjunctivitis Sicca," *Archives of Ophthalmology* 96(4):677–681 (1978).

Gobran, L., *Am. J. Physiol.* 267, L625–L633 (1994).

Gromada, J., et al., "Role of protein kinase C in the regulation of inositol phosphate production and $Ca^{2+}$ mobilization evoked by ATP and acetylcholine in rat lacrimal acini," *Eur. J. Physiol.* 429:578–586 (1995).

Grummt, F., et al., *Plant Mol. Bio.,* 2, 41 (1983).

Grymkiewicz, G. et al., "A New Generation of $Ca^{2+}$ Indicators with Greatly Improved Fluorescence Properties," J. Biol. Chem. 260(6):3440–3450 (1985).

Guranowski, A., et al., *Biochemistry,* 27, 2959 (1988).

Hiderman, R.H., et al., *J. Biol. Chem.,* 266, 6915 (1991).

Huhn, G.F., et al., *Separation and Science Technology,* 28:1959–1970 (1993).

Hussain, A1 H., et al., *Opthal. Plas. Recons. Surg.,* 9:32 (1993).

Hyde, K.J., et al., "Epidemic Keratoconjunctivitis and Lacrimal Excretory System Obstruction," *Opthamol.,* 95(10):1447–1449 (1988).

Inatomi, T., et al., "Expression of Secretory Mucin Genes by Human Conjunctival Epithelia," *Inv. Ophthamol. & Vis. Sci.* 37(8):1684–1692 (1996).

J. Physiol 447:103–18 (1992).

Kanavarioti, A., et al., *Tett. Lett.,* 32, 6065 (1991).

Kassoff, Jr., et al., "Early office–based vs late hospital–based nasolacrimal duct probing. A clinical decision analysis" *Arch. Opthalmol* 113(9):1168–1171 (1995).

Kim, B.K., et al., *Proc. Natl. Acad. Sci.,* 89, 11056 (1992).

Kimura, T., et al., *Biol. Pharm. Bull.,* 18, 1556 (1995).

Klein, G., et al., *Biochemistry,* 27, 1897 (1988).

Klein, J., *Clin. Infect. Dis.* 19, 823–33 (1994).

Knowles, M., et al., *N. Engl. J. Med.* 325, 533–38 (1991).

Lazarowski, E., et al., *Brit. J. Pharm.,* 116, 1619–27 (1995).

Lee, V., et al., *Inv. Opthal. Vis. Sci.* 38(4) (1997) abstract.

Lemp, M.A., "Is the Dry Eye Contact Lens Wearer at Risk? Yes," *Cornea* 9(1):S48–S50 (1990).

Lethem, M., et al., *Am. J. Respir. Cell Mol. Biol.* 9, 315–22 (1993).

Linberg, J.V., et al., "Primary Acquired Nasolacrimal Duct Obstruction A Clinicopathologic Report and Biopsy Technique," *Opthalmol.,* 93(8):1055–1063 (1986).

Lobaton, C.D., et al., *Eur. J. Biochem.,* 50, 495 (1975).

Lowe, G., et al., *Nucleosides & Nucleotides,* 10, 181 (1991).

Luthje, J., et al., *Eur. J. Biochem.,* 173, 241 (1988).

Mason, S., et al., *Br. J. Pharmacol.* 103, 1649–56 (1991).

Mauriello, Jr., J.A., et al., "Clinicopathologic Study of Lacrimal Sac and Nasal Mucosa in 44 Patients with Complete Acquired Nasolacrimal Duct Obstruction," *Opthalmic Plastic & Reconstructive Surgery,* 8(1):13–21 (1992).

McKenna, C., et al., *J. Org. Chem.* 46, 4574–76 (1980).

McLennan, A.G., et al., *Nucleic Acid Res.,* 12, 1609 (1984).

Miras–Portugal, M.T., et al., *Ann. NY Acad. Sci.,* 603, 523 (1990).

Morii, H., et al., *Eur. J. Biochem.,* 205, 979 (1992).

Moss, A. Parsons, V., *National Center for Health Statistics,* 1986:66–7, DHHS Publication No. (PHS) 86–1588 (1985).

Ng, K.E., et al., *Nucleic Acid Res.,* 15, 3573 (1987).

Noone, P., et al., *Am. J. Respir. Crit. Care Med.* 153, A530 (1996).

Olivier, K., et al.,*Am. J. Respr. Crit. Care Med.* 154, 217–23 (1996).

Panchenko, V.A., et al., *Neuroscience,* 70, 353 (1996).

Pintor, J., et al., *Br. J. Pharmacol.* 115, 895 (1995).

Pintor, J., et al., *J. Neurochem.,* 64, 670 (1995).

Pohl, U., et al. *Fed. Amer. Soc. Exper. Bio.,* Abstr. Part. I, No. 1878 (1991).

Portzback, R.K., et al., *Am. J. Opthal.,* 94:585 (1982).

Rapaport, E., et al., *Proc. Natl. Acad. Sci.,* 78, 838 (1981).

Rotilan, P., et al., *FEBS,* 280, 371 (1991).

Sasaki, T. et al., "Extracellular ATP activates receptor–operated cation channels in mouse lacrimal acinar cells to promote calcium influx in the absence of phosphoinositide metabolism", *FEBS* 264(1):130–134 (1990).

Sasaki, T., et al., "The ATP–induced inward current in mouse lacrimal acinar cells is potentiated by isoprenaline and GTP," *P. Physiol.* 447:103–118 (1992).

Schulze–Lohoff, E., et al., *Hypertension,* 26, 899 (1995).

Shermetaro, C., et al., "Adult nasolacrimal duct obstruction," *JAOA* 94(3):229–232 (1994).

Sillero, M.A.G., et al., *Eur. J. Biochem.,* 76, 331 (1977).

Silverman, R.H., et al., *Microbiological Rev.,* 43, 27 (1979).

Stepinski, J., et al., *Nucleosides & Nucleotides,* 14, 717 (1995).

Tarbet, K.J., et al., "External Dacryocystorhinostomy Surgical Success, Patient Satisfaction, and Economic Cost", *Opthalmol.,* 102(7):1065–1070 (1995).

Vallejo, et al., "Dinucleosidasetetraphosphatase in Rat Liver and *Artemia Salina",* Biochimica et Biophysica Acta, 438:304–309 (1976).

Vincent, P., "Cationic channels sensitive to extracellular ATP in rat lacrimal cells," *J. Physiol.* 499:313–331 (1992).

Visscher, J., et al., "Selective cleavage of pyrophosphate linkages," *Nucleic Acids Research* 20 (21): 5749–5752, 1992.

Walker, J., et al., *Biochemistry,* 32, 14009 (1993).

Young, J.D.H., et al., "Congenital nasolacrimal duct obstruction in the second year of life: a multicentre trial of management," *Eye,* 10:485–491 (1996).

Zamecnik, P., et al., *Analytical Biochem.,* 134, 1 (1983).

Zamecnik, P.C., et al., *Proc. Natl. Acad. Sci.,* 89, 2370 (1992).

Zatorski, A., et al., *J. Med. Chem.,* 39, 2422 (1996).

\* cited by examiner

METHOD OF TREATING DRY EYE DISEASE WITH PURINERGIC RECEPTOR AGONISTS

This application is a continuation-in-part of U.S. application Ser. No. 10/010,055, filed Nov. 9, 2001; which is a continuation of U.S. application Ser. No. 09/171,169, filed Oct. 14, 1998; which was the National Stage of International Application No. PCT/US98/02701, filed Feb. 6, 1998, published Aug. 13, 1998 under PCT Article 21(2) in English; and was a continuation-in-part of U.S. application Ser. No. 08/797,472 filed Feb. 6, 1997 now U.S. Pat. No. 5,900,407.

TECHNICAL FIELD

This invention relates to a method of regulating secretions in and around the eye of a patient by administering purinergic receptor agonists such as certain uridine, adenine, or cytidine triphosphates as well as other dinucleoside polyphosphate compounds.

This invention also relates to a method of enhancing drainage of the lacrimal system by administering a pharmacologic agent that enhances mucociliary clearance of the nasolacrimal duct of a mammal. These agents include certain uridine, adenine and cytidine triphosphates as well as other dinucleoside polyphosphate compounds.

BACKGROUND OF THE INVENTION

There are many situations where it is therapeutically desirable to increase the amount of tear fluid produced by the eye. Dry eye disease is the general term for indications produced by abnormalities of the precorneal tear film characterized by a decrease in tear production or an increase in tear film evaporation, together with the ocular surface disease that results. Approximately 38 million Americans are affected with some type of dry eye disorder. Among the indications that are referred to by the general term "dry eye disease" are: keratoconjunctivitis sicca (KCS), age-related dry eye, Stevens-Johnson syndrome, Sjogren's syndrome, ocular cicatrical pemphigoid, blepharitis, corneal injury, infection, Riley-Day syndrome, congenital alacrima, nutritional disorders or deficiencies (including vitamins), pharmacologic side effects, eye stress and glandular and tissue destruction, environmental exposure to smog, smoke, excessively dry air, airborne particulates, autoimmune and other immunodeficient disorders, and comatose patients rendered unable to blink.

A healthy precorneal tear film has several important functions: 1) to protect the cornea from desiccation; 2) to aid in the immune response to infections; 3) to enhance oxygen permeation into the cornea; and 4) to allow gliding movement of the eyeball and eyelids. There are two structures responsible for maintaining the properties of the tear film—the lacrimal glands and the conjunctiva (the mucous membrane which surrounds part of the eyeball and inner eyelids). These structures maintain the tear film via regulation of water and electrolyte transport and via mucin release by goblet cells.

The progression of dry eye disease is characterized by four main "milestones." The first milestone is a decrease in tear production. In rabbit models, this decrease in tear production has been shown to correlate with an increase in tear osmolarity. The second milestone is a loss of mucous-containing conjunctival goblet cells. This decrease in goblet cell density becomes evident several weeks after the onset of decreased tear production. The third milestone in the progression of dry eye disease occurs about 1 year later when desquamation of the corneal epithelium is observed. The fourth and last milestone of the disease is a destabilization of the cornea-tear interface (Gilbard, *CLAO Journal*, 22(2), 141–45 (1996)).

Currently, the pharmaceutical treatment of dry eye disease is mostly limited to administration of artificial tears (saline solution) to temporarily rehydrate the eyes. However, relief is short-lived and frequent dosing is necessary. In addition, artificial tears often have contraindications and incompatibility with soft contact lenses (Lemp, *Cornea*, 9(1), S48–550 (1990)). The use of phosphodiesterase inhibitors, such as 3-isobutyl-1-methylxanthine (IBMX) to stimulate tear secretion is disclosed in U.S. Pat. No. 4,753,945. The effectiveness of these phosphodiesterase inhibitors is currently being investigated (Gilbard, et al., *Arch. Ophthal*, 112, 1614–16 (1994) and 109, 672–76 (1991); idem, *Inv. Ophthal. Vis. Sci.* 31, 1381–88 (1990)). Stimulation of tear secretion by topical application of melanocyte stimulating hormones is described in U.S. Pat. No. 4,868,154.

There are many situations where it is therapeutically desirable to increase drainage of the lacrimal system. The lacrimal system has two functioning components: the secretory part, which produces tears, and the excretory part, which drains the tears into the nose. When the lacrimal drainage system is not functioning properly the result can be excessive tearing (epiphora), mucopurulent discharge, and recurrent dacryocystitis (Shermataro, et al., *JAOA*, 94, 229 (1994)). In fact, tearing is one of the most common complaints that brings a patient to the ophthalmologist's office (Conway, *Ophthal. Plas. Reconstr. Surg.*, 10, 185 (1994)).

The most common malfunction of the lacrimal drainage system is nasolacrimal duct obstruction, which results in stasis of tears in the lacrimal sac. The accumulation of fluid and mucus results in tearing and expulsion of mucopurulent material, causing the eyelids to be "stuck together" on awakening in the morning. The lack of clearance of the tear fluid also leads to inflammation and chronic infection of the lacrimal sac and ducts (Hyde, et al., *Ophthal.*, 95, 1447 (1988); Blicker, et al., *Ophthal. Plas. Reconstr. Surg.*, 9, 43 (1993); Mauriello Jr., et al., *Ophthal. Plast. Reconstr. Surg.*, 8, 13 (1992)).

Nasolacrimal duct obstruction can be divided into two etiologic classes: primary acquired nasolacrimal duct obstruction (PANDO), which is characterized by hyperplasia and fibrosis of the mucosal epithelium, and secondary acquired nasolacrimal duct obstruction (SANDO), which is caused by cancer, inflammation, infection, trauma and mechanical problems (Bartley, *Ophthal. Plast. Reconstr. Surg.*, 8, 237 (1992)). An occluded nasolacrimal duct is more common in middle-aged women and infants. In fact, up to 20% of all infants are affected by nasolacrimal duct obstruction with most of them becoming symptom free by their first birthday (Young, et al., *Eye*, 10, 485 (1996)).

Current treatments for nasolacrimal duct obstruction are mostly invasive or surgical procedures that vary in aggressiveness. Intervention can take the form of probing the duct with a fine catheter; however, this is a difficult and delicate procedure that requires special training and equipment (Kassoff, et al., *Arch. Ophthal.*, 113, 1168 (1995); Griffiths, U.S. Pat. Nos. 4,921,485 (1990) and 5,062,831 (1991); Becker, et al., U.S. Pat. Nos. 5,021,043 (1991) and 5,169, 386 (1992)). In some cases silastic intubation of the nasolacrimal duct increases drainage of tears through the nasolacrimal duct (Dortzbach, et al., *Amer. J Ophthal.*, 94, 585 (1982); Al-Hussain, et al., *Ophthal. Plas. Reconstr. Surg.*, 9, 32 (1993); Crawford, et al. U.S. Pat. No. 4,380,239 (1983); Ector, Jr., U.S. Pat. No. 4,658,816 (1987)). A more aggressive procedure is a dacryo-cystorhinostomy which surgically creates a new drainage path above the sight of obstruction allowing continuity between the lacrimal sac and the nasal cavity (Linberg, et al., *Ophthal.*, 93, 1055 (1986); Tarbert, *Ophthal.*, 102, 1065 (1995); O'Donnell, Jr., U.S. Pat. No. 5,345,948 (1994)). External massage of the nasolacrimal duct has also been shown to increase tear transit times through the nasolacrimal duct (J. A. Foster, et al., *Ophthal. Plas. Reconstr. Surg.*, 12, 32 (1996)).

Thus, as a result of the ineffectiveness and inconvenience of current therapies, medical researchers have sought to develop alternatives for the treatment of dry eye disorders and nasolacrimal duct disorders. It has been shown that uridine 5'-triphosphate (UTP) and adenine 5'-triphosphate (ATP) are potent agonists of $P2Y_2$ purinergic receptors found on the surface of human airway epithelium. Activation of these $P2Y_2$ purinergic receptors induces chloride and water secretion, helping hydrate the airway surface secretions. Use of UTP and ATP for the purpose of treating pulmonary disorders characterized by the retention of lung mucus secretions is described in U.S. Pat. No. 5,292,498. Because of the demonstrated ability of UTP to increase hydration of airway epithelial secretions, applicants were motivated to investigate whether UTP and other $P2Y_2$ and $P2Y_4$ purinergic receptor agonists could also stimulate hydration of ocular epithelia.

It had previously been shown that P2 type purinergic receptors in rat and mouse lacrimal acinar cells responded to extracellular ATP by increasing intracellular calcium (Sasaki, et al., *Febs Lett.* 264, 130–34 (1990); idem, *J. Physiol*,. 447, 103–18 (1992);Vincent, *J. Physiol.*, 449, 313–31 (1992); Gromada, et al., *Eur. J. Physiol.*, 429, 578 (1995); Lee, et al. *Inv. Ophthal. Vis. Sci.*, 38(4)(1997) abstract).

The discovery of diadenosine 5'-polyphosphates ($Ap_nA$, n=2–7) and their release from platelets and chromaffin cells has led to many studies of the biological activity and cellular processing of these intra- and extracellular signalling molecules (Pintor, *Nervous Control of the Eye*, 171–210 (1999); Hoyle et al., *Drug Dev Res*, 52:260–273 (2001)). Diadenosine polyphosphates have interesting pharmacological effects on nucleotide receptors; that is, depending on the chain length, they may be agonists or antagonists at P2X and P2Y receptors with varying selectivity. There is not a clear relationship between the phosphate chain length and the selective activity on P2X or P2Y receptors; however, from a physiological point of view, some of them can act as vasodilators ($Ap_2A$ and $Ap_3A$) while others act as vasoconstrictors ($Ap_4A$, $Ap_5A$ and $Ap_6A$) (Ralevic, et al., *Pharmacol Rev*, 50:413–492 (1998)).

Diadenosine polyphosphates were found to be potent and full agonists in cells overexpressing the human $P2Y_2$ receptor (Lazarowski et al., *Br J Pharmacol*, 116:1619–1627 (1995). The avian $P2Y_1$ receptor is sensitive to $Ap_4A$, presenting $EC_{50}$ values in the nM range (Pintor et al., *Br J Pharmacol*, 119:1006–1012 (1996). Important differences have been observed on native $P2Y_1$ receptors, where diadenosine tetraphosphate behaved as an antagonist in clear contrast with the behavior of this dinucleotide in cloned $P2Y_1$ receptors (Vigne et al., *Br J Pharmacol*, 129:1506–1512 (2000). On the other hand, other expressed P2Y receptors, such as $P2Y_4$ are also activated by $Ap_3A$–$Ap_6A$ in the micromolar range (Communi, et al.,*Eur J Pharmacol* 317:383–389 (1996); Janssens et al., *Biochem Biophys Res Commun*, 236:106–112 (1997)).

SUMMARY OF THE INVENTION

This invention is directed to a method of stimulating tear secretion and mucin production in eyes. The method comprises the step of administering to the eyes of a subject a composition comprising a compound of Formula I, II, III, or IV and its pharmaceutically acceptable salts, in an amount effective to stimulate tear fluid secretion. The method of the present invention may be used to increase tear production for any reason, including, but not limited to, treatment of dry eye disease and corneal injury.

The method of the present invention comprises topically administering a liquid or gel composition comprising an effective amount of a $P2Y_2$ and/or $P2Y_4$ purinergic receptor agonist selected from the group consisting of uridine triphosphate (UTP) and its analogs, $P^1$, $P^4$-di(uridine-5'-)tetraphosphate ($U_2P_4$) and its analogs, $P^1$, $P^4$-di(adenosine-5'-)tetraphosphate ($A_2P_4$) and its analogs, $P^1$, $P^5$-di(adenosine-5'-)pentaphosphate ($A_2P_5$) and its analogs, $P^1$, $P^6$-di(adenosine-5'-)hexaphosphate ($A_2P_6$) and its analogs, cytidine 5'-triphosphate (CTP) and its analogs, and adenosine 5'-triphosphate (ATP) and its analogs.

Yet another aspect of the present invention is a pharmaceutical composition comprising a compound of Formula I, II, III, or IV, in a pharmaceutical carrier in an amount effective to stimulate tear production or to enhance clearance of nasolacrimal ducts in a subject in need of such treatment.

DETAILED DESCRIPTION OF THE INVENTION

Figure 1:
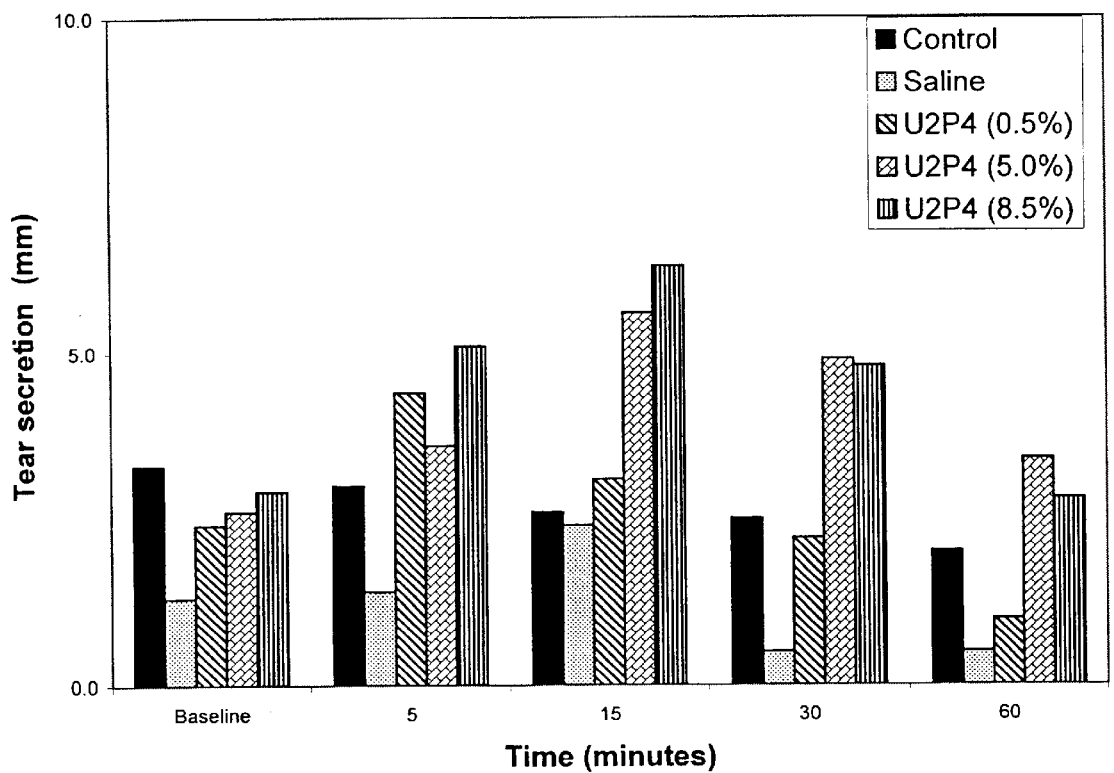
FIG. 1 shows the tear secretion effects for 60 minutes after a single dose of $U_2P_4$ at three concentrations in rabbit eyes. The data shown are the mean of eight animals.

The present invention is directed to a method of stimulating tear secretion and mucin production in eyes for any reason, including, but not limited to, treatment of dry eye disease. Dry eye disease is defined to include: keratoconjunctivitis sicca (KCS), age-related dry eye, Stevens-Johnson syndrome, Sjogren's syndrome, ocular cicatrical pemphigoid, blepharitis, corneal injury, infection, Riley-Day syndrome, congenital alacrima, nutritional disorders or deficiencies (including vitamin), pharmacologic side effects, eye stress and glandular and tissue destruction, environmental exposure to smog, smoke, excessively dry air, airborne particulates, autoimmune and other immunodeficient disorders, and comatose patients rendered unable to blink. The present invention may also be useful as a wash or irrigation solution in conscious individuals, during surgery or to maintain comatose patients or those who cannot blink due to muscle or nerve damage, neuromuscular blockade or loss of the eyelids. The present invention may also be useful for treating corneal injury.

The present invention is also directed to a method of enhancing drainage of the lacrimal system in a subject in need of such treatment. The method of this aspect of the invention may be used to enhance clearance of the nasolacrimal duct for any reason, including, but not limited to, treatment of nasolacrimal duct obstruction. Nasolacrimal duct obstruction is defined to include both primary and secondary acquired nasolacrimal duct obstruction and pediatric nasolacrimal duct obstruction. The present invention may also be useful as a nasolacrimal wash or irrigation solution in conscious individuals or during nasolacrimal duct surgery or intubation. The compounds disclosed herein may also be used in conjunction with mucolytic agents, such as DNAse, acetylcysteine and bromhexine.

The present method of stimulating tear secretion and mucin production in eyes and the present method of enhancing drainage of the lacrimal system comprise the step of administering to the eyes an effective amount of a composition comprising a compound of $P2Y_2$ and/or $P2Y_4$ purinergic receptor agonist selected from the group consisting of general Formula I, i.e., uridine triphosphate (UTP) and its analogs; general Formula II, i.e., dinucleoside polyphosphate; general Formula III, i.e., cytidine 5'-triphosphate (CTP) and its analogs; and general Formula IV, i.e., adenosine 5'-triphosphate (ATP) and its analogs, with the compound of Formula I, II, III or IV administered in an amount effective to stimulate tear secretion or to enhance clearance of nasolacrimal duct obstruction.

Applicant has discovered that tear secretion can be stimulated from lacrimal accessory tissues via $P2Y_2$ and/or $P2Y_4$ purinergic receptor-mediated mechanisms similar to those which hydrate airway epithelia. Applicant has also discovered that stimulators of mucociliary clearance when applied topically to the eye or injected into the nasolacrimal drainage system increases the flow of tears through the nasolacrimal duct and hence relieves the symptoms associated with nasolacrimal duct obstruction.

Active Compounds Useful for the Invention

UTP and its analogs are depicted in general Formula I:

Formula I

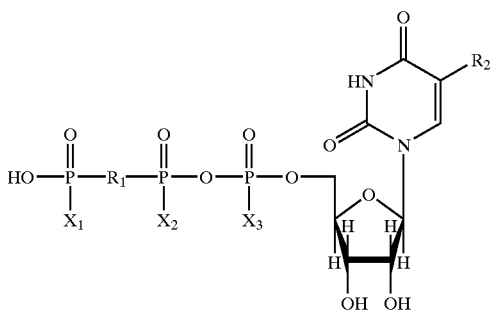

wherein:
$X_1$, $X_2$ and $X_3$ are each independently either $O^-$ or $S^-$. Preferably, $X_2$ and $X_3$ are $O^-$.
$R_1$ is O, imido, methylene or dihalomethylene (e.g., dichloromethylene or difluoromethylene). Preferably, $R_1$ is oxygen or imido.

$R_2$ is H or Br. Preferably, $R_2$ is H. Particularly preferred compounds of Formula I are uridine 5'-triphosphate (UTP) and uridine 5'-O-(3-thiotriphosphate) (UTPγS).

A dinucleotide is depicted by the general Formula II:

FORMULA II

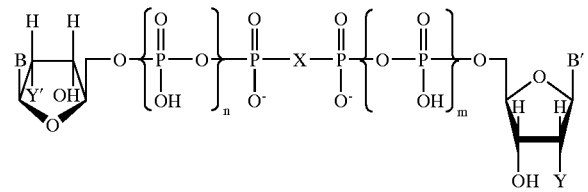

wherein:
X is oxygen, imido, methylene or difluoromethylene;
Y is H, or OH;
Y' is H, or OH;
n=0, 1, or 2;
m=0, 1, or 2;
n+m=0–4; and
B and B' are each independently a purine residue, as in Formula IIa, or a pyrimidine residue, as in Formula IIb, linked through the 9- or 1-position, respectively. In the instance where B and B' are uracil, attached at the N–1 position to the ribosyl moiety, then the total of m+n may equal 3 or 4 when X is oxygen. The ribosyl moieties are in the D-configuration, as shown, but may also be L-, or D- and L-. The D-configuration is preferred.

FORMULA IIa

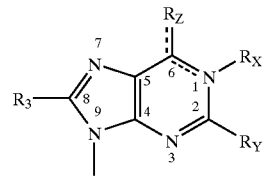

wherein:
$R_X$ is O, H or is absent;
$R_Y$ is hydrogen, chlorine, amino, monosubstituted amino, disubstituted amino, alkylthio, arylthio, or aralkylthio, wherein the substituent on sulfur contains up to a maximum of 20 carbon atoms, with or without unsaturation;
$R_Z$ is oxo, mercapto, thione, alkylthio, arylthio, aralkylthio, acylthio, alkyloxy, aryloxy, aralkyloxy, acyloxy, amino, mono-substituted amino or di-substituted amino;
$R_3$ is hydrogen, azido, alkoxy, aryloxy, aralkyloxy, alkylthio, arylthio, aralkylthio, amino, mono-substituted amino, di-substituted amino, or $T(C_{1-6}alkyl)OCONH(C_{1-6}alkyl)W$ wherein T and W are independently amino, mercapto, hydroxy or carboxyl, or pharmaceutically acceptable esters, amides or salts thereof.

Formula IIa includes substituted derivatives of adenine such as adenine 1-oxide; 1, N6-(4- or 5-substituted etheno) adenine; 6-substituted adenine; or 8-substituted aminoadenine. Formula IIa also includes inosine.

When $R_3$ and $R_Z$ are independently NHR', R' is hydrogen, arylalkyl ($C_{1-6}$) groups with the aryl moiety optionally functionalized as described below; alkyl; and alkyl groups with functional groups therein, such as: ([6-aminohexyl] carbamoylmethyl)-, and ω-acylated-amino(hydroxy, thiol and carboxy) derivatives where the acyl group is chosen from among, but not limited to, acetyl, trifluroroacetyl, benzoyl, substituted-benzoyl, etc., or the carboxylic moiety is present as its ester or amide derivative, for example, the ethyl or methyl ester or its methyl, ethyl or benzamido derivative. The ω-amino(hydroxy, thiol) moiety may be alkylated with a $C_{1-4}$ alkyl group.

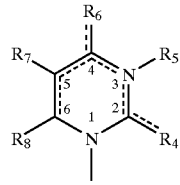

Formula IIb wherein:
- $R_4$ is hydroxy, oxo, mercapto, thione, amino, cyano, $C_{7-12}$arylalkoxy, $C_{1-6}$ alkylthio, $C_{1-6}$ alkoxy, $C_{1-6}$ alkylamino or di$C_{1-4}$alkylamino, wherein the alkyl groups are optionally linked to form a heterocycle;
- $R_5$ is hydrogen, acetyl, benzoyl, $C_{1-6}$ alkyl, $C_{1-5}$ alkanoyl, aroyl, or absent;
- $R_6$ is hydroxy, oxo, mercapto, thione, $C_{1-4}$alkoxy, $C_{7-12}$arylalkoxy, $C_{1-6}$alkylthio, S-phenyl, arylthio, arylalkylthio, triazolyl amino, $C_{1-6}$alkylamino, $C_{1-5}$ disubstituted amino, or di-$C_{1-4}$alkylamino, wherein said dialkyl groups are optionally linked to form a heterocycle or linked to form a substituted ring such as morpholino, pyrrolo; or
- $R_5$ and $R_6$ taken together form a 5-membered fused imidazole ring of 3,$N^4$-ethenocytosine derivatives between positions 3 and 4 of the pyrimidine ring, wherein said etheno moiety is optionally substituted on the 4- or 5-positions with $C_{1-4}$ alkyl, phenyl or phenyloxy; wherein at least one hydrogen of said $C_{1-4}$ alkyl, phenyl or phenyloxy is optionally substituted with a moiety selected from the group consisting of halogen, hydroxy, $C_{1-4}$ alkoxy, $C_{1-4}$ alkyl, $C_{6-10}$ aryl, $C_{7-12}$ arylalkyl, carboxy, cyano, nitro, sulfonamido, sulfonate, phosphate, sulfonic acid, amino, $C_{1-4}$ alkylamino, or di-$C_{1-4}$ alkylamino, wherein said dialkyl groups are optionally linked to form a heterocycle;
- $R_7$ is hydrogen, hydroxy, cyano, nitro, $C_{1-6}$ alkyl or phenyl, substituted $C_{2-8}$ alkynyl, halogen, substituted $C_{1-4}$ alkyl, $CF_3$, $C_{2-3}$ alkenyl, $C_{2-3}$ alkynyl, allylamino, bromovinyl, ethyl propenoate, propenoic acid or $C_{2-8}$ alkenyl; or
- $R_6$ and $R_7$ together form a 5 or 6-membered saturated or unsaturated ring bonded through N or O or S at $R_6$, such ring optionally contains substituents that themselves contain functionalities;
- $R_8$ is hydrogen, amino, di-$C_{1-4}$alkylamino, $C_{1-4}$alkoxy, $C_{7-12}$arylalkoxy, $C_{1-4}$alkylthio, $C_{7-12}$arylalkylthio, carboxamidomethyl, carboxymethyl, methoxy, methylthio, phenoxy, or phenylthio; provided that when $R_8$ is amino or substituted amino, $R_7$ is hydrogen.

In the general structure of Formula IIb above, the dotted lines in the 2- to 6-positions are intended to indicate the presence of single or double bonds in these positions; the relative positions of the double or single bonds being determined by whether the $R_4$, $R_6$ and $R_7$ substituents are capable of keto-enol tautomerism.

In the general structures of Formulae IIa and IIb above, the acyl groups include alkanoyl or aroyl groups. The alkyl groups contain 1 to 8 carbon atoms, particularly 1 to 4 carbon atoms optionally substituted by one or more appropriate substituents, as described below. The aryl groups including the aryl moieties of such groups as aryloxy are preferably phenyl groups optionally substituted by one or more appropriate substituents, as described below. The above mentioned alkenyl and alkynyl groups advantageously contain 2 to 8 carbon atoms, particulary 2 to 6 carbon atoms, e.g., ethenyl or ethynyl, optionally substituted by one or more appropriate substituents as described below. Appropriate substituents on the above-mentioned alkyl, alkenyl, alkynyl, and aryl groups are selected from halogen, hydroxy, $C_{1-4}$ alkoxy, $C_{1-4}$ alkyl, $C_{7-12}$ arylalkoxy, carboxy, cyano, nitro, sulfonamido, sulfonate, phophate, sulfonic, amino and substituted amino wherein the amino is singly or doubly substituted by a $C_{1-4}$ alkyl, and when doubly substituted, the alkyl groups optionally being linked to form a heterocycle.

Previously described dinucleotide polyphosphates are listed in Table I, followed by literature references. These dinucleotide polyphosphates are useful in the present invention.

TABLE I

DINUCLEOTIDES IN THE LITERATURE

| $Np_2N$ | $Np_2N'$ | $Np_3N$ | $Np_3N'$ | $Np_4N$ | $Np_4N'$ | $Np_5N$ | $Np_5N'$ | $Np_6N$ | $Np_6N'$ |
|---|---|---|---|---|---|---|---|---|---|
| $Ap_2A$ | $Ap_2NAD$ | $Up_3U$ | $Ap_3T$ | $Up_4U$ | $Ap_4U$ | $Ap_5A$ | $Ap_5T$ | $Ap_6A$ | $Ap_6T$ |
| $Gp_2G$ | $Ap_2TAD$ | $Ap_3A$ | $m^7Gp_3G$ | $Ap_4A$ | $Ap_4C$ | $Up_5U$ | $Ap_5U$ | $Up_6U$ | $Ap_6U$ |
| $m^7Gp_2m^7G$ | $Ap_2C$-NAD | $Xp_3X$ | $m^{2,2,7}Gp_3G$ | $Cp_4C$ | $Ap_4G$ | (5-BrU)$p_5$(5-BrU) | $Ap_5$(5-BrU) | (5-BrU)$p_6$(5-BrU) | $Up_6$(5-BrU) |
| $Up_2U$ | $Ap_2C$-PAD | $m^7Gp_3m^7G$ | $m^{2,7}Gp_3G$ | $Gp_4G$ | $Gp_4U$ | $Gp_5G$ | $Up_5$(5-BrU) | $Gp_6G$ | $Ap_6$(5-BrU) |
| (5-BrU)$p_2$(5-BrU) | $Ap_2BAD$ | $Gp_3G$ | $Ap_3U$ | $Xp_4X$ | $Gp_4C$ | 2'd$Gp_5$2'dG | | | |
| (AZT)$p_2$(AZT) | $m^7Gp_2G$ | (5-BrU)$p_3$(5-BrU) | $Ap_3$(5-BrU) | $Dp_4D$ | $Up_4C$ | $Ip_5I$ | | | |
| (5FU)$p_2$(5FU) | $Ap_2G$ | $Cp_3C$ | $Up_3$(5-BrU) | $eAp_4eA$ | $Ap_4T$ | | | | |
| $Ip_2I$ | $Ap_2U$ | $Ip_3I$ | $Gp_3A$ | $m^7Gp_4m^7G$ | $m^7Gp_4G$ | | | | |
| | $Ap_2$(5-BrU) | Ap-CH$_2$-ppA | $Gp_3C$ | (5-BrU)$p_4$(5-BrU) | $m^{2,7}Gp_4G$ | | | | |
| | $Up_2$(5-BrU) | Ap-CF$_2$-ppA | $Gp_3Gm$ | $dAp_4dA$ | $m^{2,2,7}Gp_4G$ | | | | |
| | (AZT)$p_2$(5-FU) | | $Gp_3Am$ | 3'-d$Ap_4$3'-dA | (5-BrU)$p_4A$ | | | | |

TABLE I-continued

DINUCLEOTIDES IN THE LITERATURE

| Np$_2$N | Np$_2$N' | Np$_3$N | Np$_3$N' | Np$_4$N | Np$_4$N' | Np$_5$N | Np$_5$N' | Np$_6$N | Np$_6$N' |
|---|---|---|---|---|---|---|---|---|---|
| | Ap$_2$T | | m$^7$Gp$_3$m$^6$Am | dGp$_4$dG | (5-BrU)p$_4$U | | | | |
| | Gp$_2$A | | m$^7$Gp$_3$Gm | ApCH$_2$p$_3$A | Ap$_4$(8-BrA) | | | | |
| | Ip$_2$A | | Ap$_3$C | Ip$_4$I | Ap$_4$X | | | | |
| | 2dGp$_2$A | | Ap$_3$G | Ap$_2$CH$_2$p$_2$A | Ap$_4$I | | | | |
| | Ap$_2$C | | m$^7$Gp$_3$A | Ap$_2$CF$_2$p$_2$A | Ap$_4$dA | | | | |
| | | | Ip$_3$A | Dp$_2$CH$_2$p$_2$D | Ap$_4$d(5-FU) | | | | |
| | | | Ip$_3$G | Dp$_2$CF$_2$p$_2$D | Ap$_4$araA | | | | |
| | | | 2'dGp$_3$A | | Ap$_2$CH$_2$p$_2$U | | | | |
| | | | 2'dGp$_3$-2'dG | | Ap$_2$CH$_2$p$_2$G | | | | |
| | | | m$^7$Gp$_3$Am | | Ap$_3$CH$_2$pT | | | | |
| | | | Gp$_3$U | | ahaAp$_4$A | | | | |
| | | | m$^7$Gp$_3$Cm | | ahaAp$_4$G | | | | |
| | | | m$^7$Gp$_3$Um | | | | | | |
| | | | m$^7$Gp$_3$G | | | | | | |
| | | | App-CH$_2$-pT | | | | | | |
| | | | Ap-CF$_2$-ppA | | | | | | |

A = Adenosine  
U = Uridine  
G = Guanosine  
T = Thymidine  
X = Xanthosine  
TAD = Tiazofurin  
BAD = Benzamide riboside  
D = 2,6-Diaminopurine  
Gm = 2'-O-methylguanosine  
m$^6$Am = N6-methyl-2'-O-methyladenosine  
Um = 2'-O-methyluridine  
AZT = Thymine-3'-azido2', 3'-dideoxy-D-riboside  
5-BrU = 5-bromouridine  
A = Adenosine  
U = Uridine  
G = Guanosine  
T = Thymidine  
X = Xanthosine  
TAD = Tiazofurin  
BAD = Benzamide riboside  
D = 2,6-Diaminopurine eA = Ethenoadenosine  
m$^7$G = 7-Methylguanosine  
m$^{2,7}$G = 2,7-Dimethylguanosine  
m$^{2,2,7}$G = 2,2,7-Trimethylguanosine  
NAD = nicotinamide riboside  
C-NAD = C-nicotinamide riboside  
C-PAD = C-picolinamide riboside  
N = Nucleoside  
Am = 2'-O-methyladenosine  
Cm = 2'-O-methylcytidine  
aha = 8-(6-aminohexyl)  
X = Xanthosine  
5-FU = 5-fluorouridine  
eA = Ethenoadenosine  
m$^7$G = 7-Methylguanosine  
m$^{2,7}$G = 2,7-Dimethylguanosine  
m$^{2,2,7}$G = 2,2,7-Trimethylguanosine  
NAD = nicotinamide riboside  
C-NAD = C-nicotinamide riboside  
C-PAD = C-picolinamide riboside  
N = Nucleoside (1) M. A. G. Sillero et al., Eur. J. Biochem., 76, 331 (1977)
(2) C. G. Vallejo et al., Biochim. Biophys. Acta, 483, 304 (1976)
(3) H. Coste et al., J. Biol. Chem., 262, 12096 (1987)
(4) K. E. Ng et al., Nucleic Acid Res., 15, 3573 (1987)
(5) J. Stepinski et al, Nucleosides & Nucleotides, 14, 717 (1995)
(6) A. Zatorski et al., J. Med. Chem., 39, 2422 (1996)
(7) P. Rotilan et al., FEBS, 280, 371 (1991)
(8) P. C. Zamecnik et al., Proc. Natl. Acad. Sci., 89, 2370 (1992)
(9) J. Walker et al., Biochemistry, 32, 14009 (1993)
(10) R. H. Hiderman et al., J. Biol. Chem., 266, 6915 (1991)
(11) J. Luthje et al., Eur. J. Biochem., 173, 241 (1988)
(12) R. H. Silverman et al., Microbiological Rev., 43, 27 (1979)
(13) C. D. Lobaton et al., Eur. J. Biochem., 50, 495 (1975)
(14) G. Lowe et al., Nucleosides & Nucleotides, 10, 181 (1991)
(15) G. M. Blackburn et al., Nucleosides & Nucleotides, 10, 549 (1991)
(16) J. C. Baker et al., Mutation Res., 208, 87 (1988)
(17) G. Klein et al., Biochemistry, 27, 1897 (1988)
(18) E. Castro et al., Br. J. Pharmacol., 100, 360 (1990)
(19) D. R. Elmaleh et al., Proc. Natl. Acad. Sci., 81, 918 (1984)
(20) R. Bone et al., J. Biol. Chem., 261, 16410 (1986)
(21) Fed. Amer. Soc. Exper. Bio., Abstr. Part I, no. 1878 (1991)
(22) M. T. Miras-Portugal et al., Ann. NY Acad. Sci., 603, 523 (1990)
(23) A. Guranowski et al., Biochemistry, 27, 2959 (1988)
(24) F. Grummt et al., Plant Mol. Bio., 2, 41 (1983)
(25) A. G. McLennan et al., Nucleic Acid Res., 12, 1609 (1984)
(26) P. Zamecnik et al., Analytical Biochem., 134, 1 (1983)
(27) E. Rapaport et al., Proc. Natl. Acad. Sci., 78, 838 (1981)
(28) T. Kimura et al., Biol. Pharm. Bull., 18, 1556 (1995)
(29) E. Schulze-Lohoff et al., Hypertension, 26, 899 (1995)
(30) B. K. Kim et al., Proc. Natl. Acad. Sci., 89, 11056 (1992)
(31) P. C. Zamecnik et al., Proc. Natl. Acad. Sci., 89, 2370 (1992)
(32) H. Morii et al., Eur. J. Biochem., 205, 979 (1992)
(33) E. Castro et al., Pflugers Arch., 426, 524 (1994)
(34) H. Schluter et al., Nature, 367, 186 (1994)
(35) E. Castro et al., Br. J. Pharmacol., 206, 833 (1992)
(36) T. Casillas et al., Biochemistry, 32, 14203 (1993)
(37) J. Pintor et al., J. Neurochem., 64, 670 (1995)
(38) E. Castro et al., J. Biol. Chem., 270, 5098 (1995)
(39) V. A. Panchenko et al., Neuroscience, 70, 353 (1996)
(40) E. Castro et al., Br. J. Pharmacol., 100, 360 (1990)
(41) J. Pintor et al., Gen. Pharmac., 26, 229 (1995)
(42) J. Pintor et al., Br. J. Phamacol., 115, 895 (1995)
(43) A. Kanavarioti et al., Tett. Lett., 32, 6065 (1991)
(44) Stutts, M. J., III, et al. WO 96/40059
(45) Theoclitou, et al. *J Chem. Soc. Perkin Trans I*, 2009–2019 (1996)
(46) Guranowski, A., et al., *Nucleosides and Nucleotides* 14:731–734 (1995)
(47) De Flora, A., et al. WO 96/02554A1
(48) Visscher, J. et al. *Nucleic Acids Research*, 20:5749–5752 (1992)
(49) Holler, E.; Holmquist, B, et al., *Biochemistry*, 22:4924–4933(1983)

(50) Orr, R. M.; et al., *Biochem. Pharmacol*.673–677 (1988)
(51) Plateau, P., Fromant, et al., *Biochemistry*, 24:914–922 (1985)
(52) Hagmeier, E., et al., *Journal of Chromatography*, 237:174–177 (1982)
(53) Scheffzek, K, et al., *Biochemistry*, 35:9716–9727 (1996)
(54) Stridh, S., et al., *Antiviral Research*, 97–105 (1981)
(55) Tarusova, N. B., et al., *Zh. Org. Khim.*, 24(7), 1474–1480 (Russian); through *Chem. Abs.* 110:154770 (1988)
(56) Hata, T., et al., *Chem. Lett.*, 987–990 (1976)
(57) Huhn, G. F., et al., *Separation Science and Technology*, 28:1959–1970 (1993);
(58) Tumanov, Yu. V., et al., *.Bioorg. Khim.*, 13:921–927 (Russian); through *Chem Abs.*, 109:6867d (1987)
(59) Devash, Y., U.S. Pat. No. 4,855,304
(60) Pintor, J., et al., *Molecular Pharmacology*, 51:277–284 (1997)
(61) Stutts et al., U.S. Pat. No. 5,635,160.

Preferred Formula II compounds for this invention are $P^1$, $P^4$-di(uridine-5'-)tetraphosphate ($U_2P_4$), $P^1$, $P^4$-di(adenosine 5'-)tetraphospate ($Ap_4A$), $P^1$, $P^5$di(adenosine-5'-)pentaphosphate ($Ap_5A$), $P^1$, $P^4$-di(adenosine 5'-)tetraphosphate ($Ap_6A$), $P^1$-(cytidine 5'-) $P^4$-(uridine 5')-tetraphosphate ($Cp_4U$), $P^1$-(deoxycytidine 5'-) $P^4$-(uridine 5')-tetraphosphate ($dCp_4U$), $P^1$-(bromophenyletheneocytidine 5'-) $P^4$-(uridine 5'-) tetraphosphate, and $P^1$-(inosine 5-) $P^4$-(uridine 5'-) tetraphosphate ($IP_4U$).

ATP and its analogs are depicted by general Formula III:

Formula III

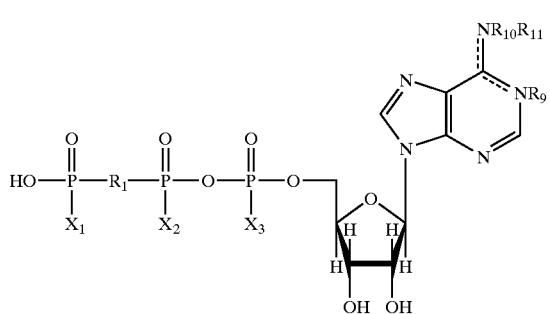

wherein:

$R_1$, $X_1$, $X_2$ and $X_3$ are defined as in Formula I.

$R_9$ is O, H or absent;

$R_{10}$ and $R_{11}$ are H while $R_9$ is absent and there is a double bond between N-1 and C-6 (adenine), or $R_{10}$ and $R_{11}$ are H while $R_9$ is 0 and there is a double bond between N-1 and C-6 (adenine 1-oxide), or $R_9$, $R_{10}$ and $R_{11}$ taken together are —CH=CH—, forming a ring from N-6 to N-1 with a double bond between N-6 and C-6 (1,N6-ethenoadenine).

CTP and its analogs are depicted by general Formula IV:

Formula IV

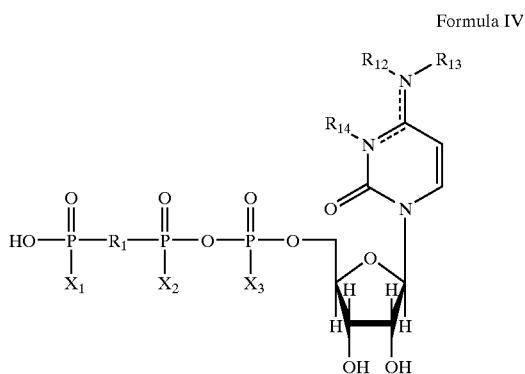

wherein:

$R_1$, $X_1$, $X_2$ and $X_3$ are defined as in Formula I.

$R_{12}$ and $R_{13}$ are H while $R_{14}$ is nothing and there is a double bond between N-3 and C-4 (cytosine), or $R_{12}$, $R_{13}$ and $R_{14}$ taken together are —CH=CH—, forming a ring from N-3 to N-4 with a double bond between N-4 and C-4 (3,$N^4$-ethenocytosine) optionally substituted at the 4- or 5-position of the etheno ring.

For simplicity, Formulae I, II, III and IV herein illustrate the active compounds in the naturally occurring D-configuration, but the present invention also encompasses compounds in the L-configuration, and mixtures of compounds in the D- and L-configurations, unless otherwise specified. The naturally occurring D-configuration is preferred.

The active compounds of the invention may also be present in the form of their pharmaceutically acceptable salts, such as, but not limited to, an alkali metal salt such as lithium, sodium or potassium; an alkaline earth metal salt such as manganese, magnesium or calcium; or an ammonium or tetraalkyl ammonium salt, i.e., $NX_4^+$ (wherein X is $C_{1-4}$). Pharmaceutically acceptable salts are salts that retain the desired biological activity of the parent compound and do not impart undesired toxicological effects.

Applicant has discovered that compounds of Formulae I–IV are potent agonists for purinergic receptors found in lacrimal gland and conjunctival preparations. The method of the present invention is an improvement upon the current most commonly used treatment of dry eye disease—artificial tears (i.e., saline solution) because the present method stimulates a patient's own tear production and secretion, which maintain natural protective and lubricant characteristics, and enhance healing of corneal injuries. Furthermore, the method of the present invention may be useful even where lacrimal glands are dysfunctional or absent. In addition, the method of the present invention useful in enhancing clearance of obstructed nasolacrimal ducts.

The present invention is concerned primarily with the treatment of human subjects, but may also be employed for the treatment of other mammalian subjects, such as dogs and cats, for veterinary purposes.

Methods of Administration

The active compounds disclosed herein may be administered to the eyes of a patient by any suitable means, but are preferably administered by administering a liquid or gel suspension of the active compound in the form of drops, spray or gel. Alternatively, the active compounds may be applied to the eye via liposomes. Further, the active compounds may be infused into the tear film via a pump-catheter system. Another embodiment of the present invention involves the active compound contained within a continuous or selective-release device, for example, membranes such as, but not limited to, those employed in the pilocarpine (Ocusert™) System (Alza Corp., Palo Alto, Calif.). As an additional embodiment, the active compounds can be contained within, carried by, or attached to contact lenses which are placed on the eye. Another embodiment of the present invention involves the active compound contained within a swab or sponge which can be applied to the ocular surface. Another embodiment of the present invention involves the active compound contained within a liquid spray which can be applied to the ocular surface. Another embodiment of the present invention involves an injection of the active compound directly into the lacrimal tissues or onto the eye surface.

The quantity of the active compound included in the topical solution is an amount sufficient to achieve dissolved concentrations of the active compound on the ocular surface of the subject of from about $10^{-7}$ to about $10^{-1}$ moles/liter, and more preferably from about $10^{-6}$ to about $10^{-1}$ moles/liter, in order to stimulate tear secretion or enhance clearance of nasolacrimal ducts.

Depending upon the solubility of the particular formulation of active compound administered, the daily dose to promote tear secretion or enhance clearance of nasolacrimal duct clearance may be divided among one or several unit dose administrations. The total daily dose for $U_2P_4$ (for example) may range from a regimen of 2 to 6 administrations per day of a solution with a concentration of 0.25 mg/ml to 50 mg/ml, depending upon the age and condition of the subject.

Some compounds of Formula I, III and IV can be made by methods which are well known to those skilled in the art; some are commercially available, for example, from Sigma Chemical Company, PO Box 14508, St. Louis, Mo. 63178. Compounds of Formula II can be made in accordance with known procedures, or variations thereof which will be described by: P. Zamecnik, et al., *Proc. Natl. Acad. Sci. USA* 89, 838–42 (1981); and K. Ng and L. E. Orgel, *Nucleic Acids Res.* 15(8), 3572–80 (1977).

The topical solution containing the active compound may also contain a physiologically compatible vehicle, as those skilled in the ophthalmic art can select using conventional criteria. The vehicles may be selected from the known ophthalmic vehicles which include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

In addition to the topical method of administration described above, there are various methods of administering the active compounds of the present invention systemically. One such means would involve an aerosol suspension of respirable particles comprised of the active compound, which the subject inhales. The active compound would be absorbed into the bloodstream via the lungs or contact the lacrimal tissues via nasolacrimal ducts, and subsequently contact the lacrimal glands in a pharmaceutically effective amount. The respirable particles may be liquid or solid, with a particle size sufficiently small to pass through the mouth and larynx upon inhalation; in general, particles ranging from about 1 to 10 microns, but more preferably 1–5 microns, in size are considered respirable.

Another means of systemically administering the active compounds to the eyes of the subject would involve administering a liquid/liquid suspension in the form of eye drops or eye wash or nasal drops of a liquid formulation, or a nasal spray of respirable particles which the subject inhales. Liquid pharmaceutical compositions of the active compound for producing a nasal spray or nasal or eye drops may be prepared by combining the active compound with a suitable vehicle, such as sterile pyrogen free water or sterile saline by techniques known to those skilled in the art.

Other means of systemic administration of the active compound would involve oral administration, in which pharmaceutical compositions containing compounds of Formula I, II, III or IV are in the form of tablets, lozenges, aqueous or oily suspensions, dispersible powders or granules, emulsion, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Additional means of systemic administration of the active compound to the eyes of the subject would involve a suppository form of the active compound, such that a therapeutically effective amount of the compound reaches the eyes via systemic absorption and circulation.

Further means of systemic administration of the active compound would involve direct intra-operative instillation of a gel, cream, or liquid suspension form of a therapeutically effective amount of the active compound.

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be apparent to those skilled in the art of organic synthesis as well as the conditions necessary to attach and remove such groups.

The invention is illustrated further by the following examples which are not to be construed as limiting the invention in scope or spirit to the specific procedures described in it. In vivo examples in accordance with the invention are conducted on rabbits eyes. Clinical studies with patients afflicted with dry eye disease provide evidence of therapeutic efficacy in humans.

EXAMPLES

Example 1
Effects of $U_2P_4$ on Tear Secretion in Rabbits $U_2P_4$ ($P^1,P^4$-Di(uridine 5'-)tetraphosphate, tetrasodium salt) was formulated as an isotonic aqueous solution and topically administered to the eyes of albino rabbits and tear secretion experiments were conducted as a measure of efficacy in normal rabbits.

Healthy, male, adult albino New Zealand rabbits (range 2–2.5 kg) were used for these studies. Rabbits were obtained from Elevage Scientifique des Dombes (Chantillon sur Charlaronne, France). Animals were observed daily for signs of ill health and only healthy animals with no ocular abnormalities were used for experiments. Animals were housed in standard cages in one room under controlled environmental conditions. Animals had free access to food and water throughout the study. The test article for all studies was daily formulated in water and NaCl to make an isotonic solution.

$U_2P_4$ at 0.5%, 5.0% and 8.5% concentrations was instilled (50 µL) 5 times a day for 14 days into the conjunctival sac of eight rabbits in separate groups. Tear secretion was measured using a Schirmer test strip at 0, 5, 15, 30 and 60 minutes after the first and last instillation of the day on days 1, 7 and 14. The results are compared to separate saline and untreated control groups.

All three concentrations of $U_2P_4$ increased tear secretion in rabbit eyes over a 60-minute period as compared to saline control (see FIG. 1).

Example 2
Effects of $U_2P_4$, $dCp_4U$ and p-Br-Phenyl-ethenoCp$_4$U on Schirmer Scores in Rabbits This study was designed to investigate the effects of three synthetic P2Y$_2$ receptor agonists, $U_2P_4$, $dCp_4U$, and p-Br-phenyl-ethenoCp$_4$U, on tear fluid secretion following a single instillation in albino rabbits.

Each of three cohorts of rabbits (10 animal/cohort) was given a single 50 µL instillation of isotonic and pH-neutral solution of 50 mM $U_2P_4$, $dCp_4U$, and p-Br-phenyl-ethenoCp$_4$U, in one eye per animal. The contralateral eye was untreated. A fourth control cohort was given isotonic saline in one eye and untreated in the contralateral eye. Tear secretion was measured using Schirmer strips placed into each eye for 15 seconds at baseline (3 hr before first instillation) and at 10 min, 0.5, 1, 2, and 3 hr post-instillation.

Figure 2:
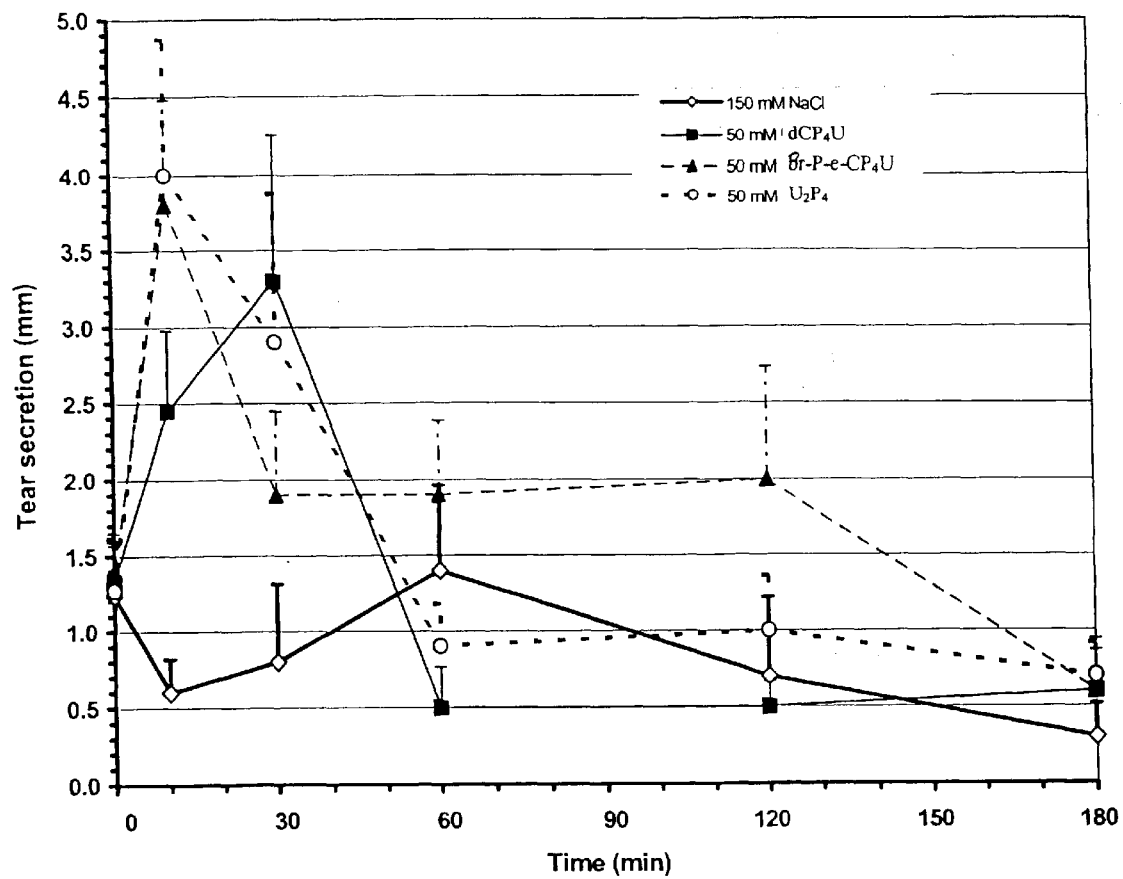
FIG. 2 shows the effects of $dCp_4U$, p-Br-phenyl-ethenoCp$_4$U, and $U_2P_4$ on Schirmer scores in rabbits.

$U_2P_4$, $dCp_4U$, and p-Br-phenyl-ethenoCp$_4$U, significantly increased Schrimer scores following topical instillation when compared with saline or untreated controls. At 10 minutes post-dosing, the rank order of potency is (highest to lowest): $U_2P_4 \approx$p-Br-Phenyl-ethenoCp$_4$U>dCp$_4$U. At 30 minutes post-dosing, the rank order of potency is: $dCp_4U \approx U_2P_4$>p-Br-Phenyl-ethenoCp$_4$U. Tear secretion from $U_2P_4$- and $dCp_4U$-treated eyes returned to pretreatment levels by 1 hour post-dosing, whereas tear secretion from p-Br-phenyl-ethenoCp$_4$U-treated eyes remained slightly elevated for up to 2 hours. The only statistically significant difference among the three treatment groups was at 1 hour post-treatment, when p-Br-phenyl-ethenoCp$_4$U showed significantly higher Schirmer scores than $dCp_4U$. (see FIG. 2.)

The results showed that three synthetic P2Y$_2$ receptor agonists $U_2P_4$, $dCp_4U$, and p-Br-phenyl-ethenoCp$_4$U, all stimulated tear secretion in rabbits.

Example 3
Dose Ranging Efficacy Trial of $U_2P_4$ Ophthalmic Solution, in Patients with Dry Eye This study was designed to compare the efficacy and safety of 4 concentrations (0.5, 1.0, 2.0 and 5.0%) of $U_2P_4$ ($P^1,P^4$-Di(uridine 5'-) tetraphosphate, tetrasodium salt) ophthalmic solution vs. placebo in 158 patients with dry eye disease.

Following a one-week placebo lead-in 158, eligible patients (Schirmer tests≦7 mm, evidence of corneal staining, and at least 2 of 5 symptoms) were randomized to one of the 4 concentrations of $U_2P_4$ or placebo for a 4-week treatment. At 4 weeks, 50% of patients receiving $U_2P_4$ were re-randomized (masked) back to placebo. Patients were evaluated at weeks 1, 2, 3, 4, 6 and 1 week post treatment and daily diary cards were completed.

One hundred and forty seven patients completed the trial at 12 centers in the United States. The final population had a mean age of 63 years and most patients were female. The percent change from baseline for the objective parameters of corneal fluorescein and the subjective parameters of itching eye and burning/painful eye for the placebo (P) group, low dose (L) group (0.5 and 1.0%) and high dose (H) group (2.0 and 5.0%) at weeks 4 and 6 are shown in Table 1 (a negative change indicates improvement):

TABLE 1

Change of Objective and Subjective Parmeters.

| | Week 4 | | | Week 6 | | |
|---|---|---|---|---|---|---|
| | P (n = 52) | L (n = 50) | H (n = 47) | P (n = 52) | L (n = 23) | H (n = 26) |
| Corneal Staining | −23% | −42%* | −32% | −26% | −46% | −44% |
| Itching Eye | 1% | −15% | −12% | −6% | −24% | −26% |
| Burning/ Painful Eye | −2% | −12% | −17% | −10% | −30% | −28% |

*p < 0.05 vs. P (Dunnetts ANCOVA)

The results showed the $U_2P_4$ ophthalmic solution had greater efficacy than placebo on both objective and subjective parameters of dry eye and is a promising new potential therapy for this disease.

Example 4
Effects of Diadenosine Polyphosphates on Rabbit Tear Production in vivo and on Human P2Y Receptors in vitro Materials UTP and ATP were purchased from Amersham Pharmacia Biotech (Piscataway, N.J.); UDP, Ap$_2$A, Ap$_3$A, Ap$_4$A, Ap$_5$A, Ap$_6$A and phosphodiesterase were purchased from Sigma Chemical. Co. (St. Louis, Mo.); 2MeSADP, PPADS, were purchased from Research Biochemicals International. (Natick, Mass.). The purity of all nucleotide agonists was established by HPLC (95–99% purity). Schirmer strips were provided by Allergan (Spain). Fluo-3-AM was obtained from Molecular Probes (Eugene, Oreg.). Dulbecco's modified Eagle's medium (DMEM), fetal bovine serum G-418, and other cell culture reagents were obtained from the Tissue Culture Facility at the University of North Carolina, or from Gibco-BRL Life Technologies (Rockville, Md.). 1321N1 human astrocytoma cells stably expressing the $P2Y_1$, $P2Y_2$, $P2Y_4$, $P2Y_6$ or $P2Y_{11}$ receptors, and wild-type 1321N1 cell were obtained from the University of North Carolina at Chapel Hill.

Animals

Male New Zealand white rabbits weighing 2.0 to 2.5 kg were placed in individual cages with free access to food and water and subjected to regular cycles of light-darkness (12 hours). All the experiments were performed according to ARVO Statement for the Use of Animals in Ophthalmic and Vision Research and to the European Directive 86/609/EEC.

Measurement of Tear Secretion

Tear secretion was measured according to the Schirmer test. Briefly, 10 $\mu$l of the test compound at the indicated concentrations were instilled via pipette in the eye. Thirty seconds after, a Schirmer strip was placed in the inferior lid margin of the eye for 5 min. Control experiments were performed by applying 10 $\mu$l of saline solution (NaCl 0.9%). Tear secretion was measured as the length (mm) of the strip wetted by the tears.

Dosing

Single-dose experiments were carried out by applying 10 $\mu$l of the corresponding nucleotide or dinucleotide at a concentration of 10 $\mu$g/$\mu$l. Dose-response analysis was performed by instilling doses ranging from $10^{-10}$ to $10^{-4}$ g/$\mu$l, always in a volume of 10 $\mu$l. Concentration-response curves were done by applying different doses in a non-cumulative fashion in one of the rabbit eyes, with the contralateral eye receiving the same volume of saline solution (control). Transformation of g/$\mu$l units into molar concentrations was performed by factoring in the corresponding molecular weight of each dinucleotide for each data point. The values presented are the means ±S.E.M. of 8 to 12 experiments performed in 36 different animals. Statistical significance between treated and non-treated animals was estimated by the Student's t-test.

Cell Culture

1321N1 human astrocytoma cells stably expressing the human $P2Y_1$, $P2Y_2$, $P2Y_4$, $P2Y_6$, and $P2Y_{11}$ receptors were grown in DMEM containing 4.5 g/l glucose, 5% fetal bovine serum and 600 $\mu$g/ml G-418. For intracellular $Ca^{2+}$ measurements, cells were seeded in 96-well black wall/clear bottom culture plates (#3904 Corning Inc., Corning, N.Y.), at a density of 35,000 cells per well and assays conducted 2 days later when the cells had reached confluence.

Intracellular $Ca^{2+}$ Measurements

On the day of the assay, the growth medium in the culture plates was aspirated and replaced with 2.5 $\mu$M Fluo-3-AM in a final volume of 50 $\mu$l and incubated for one hour at 25° C. Then, the dye was replaced with assay buffer (10 mM KCl, 118 mM NaCl, 2.5 mM $CaCl_2$, 1 mM $MgCl_2$, 10 mM glucose, and 20 mM HEPES, pH 7.4), using a Columbus Plate Washer, (Tecan Inc., Research Triangle Park, N.C.). Intracellular $Ca^{2+}$ levels in response to P2Y receptor agonists was monitored as changes in fluorescence intensity using a Fluorescent Light Imaging Plate Reader (FLIPR) (Pendergast et al., 2001) from Molecular Devices (Sunnyvale, Calif.). Average Fluorescence Units (AFU) corresponding to peak height were captured on disk and exported for further analysis. Changes in fluorescence data corresponding to concentrations of intracellular $Ca^{2+}$ were normalized to the response of the cognate agonists (2MeSADP for $P2Y_1$ receptor, ATP for $P2Y_2$ receptor, UTP for $P2Y_4$ receptor, UDP for $P2Y_6$ receptor, and ATP for $P2Y_{11}$ receptor).

Agonist potencies were calculated using a four-parameter logistic equation and the GraphPad software package (San Diego, Calif.). $EC_{50}$ values (mean±standard error) represent the concentration of agonist at which 50% of the maximal effect is achieved. Three experiments using triplicate assays were conducted on separate days for each P2Y receptor subtype.

In order to determine whether or not mononucleotides were able to modify rabbit tear secretion, single doses of ATP, UTP, ADP and UDP were instilled via pipette at 10 $\mu$g/$\mu$l (final volume 10 $\mu$l). Thirty seconds after, a Schirmer strip was placed in the inferior lid margin of the eye for 5 minutes. Control experiments were performed by applying 10 $\mu$l of saline solution (NaCl 0.9%). Tear secretion was measured as the length (mm) of the strip wetted by the tears and values were expressed as percent saline control (*P<0.001; P<0.05) compared to saline solution (Student's t-test).

Tear Secretion Results

Figure 3:
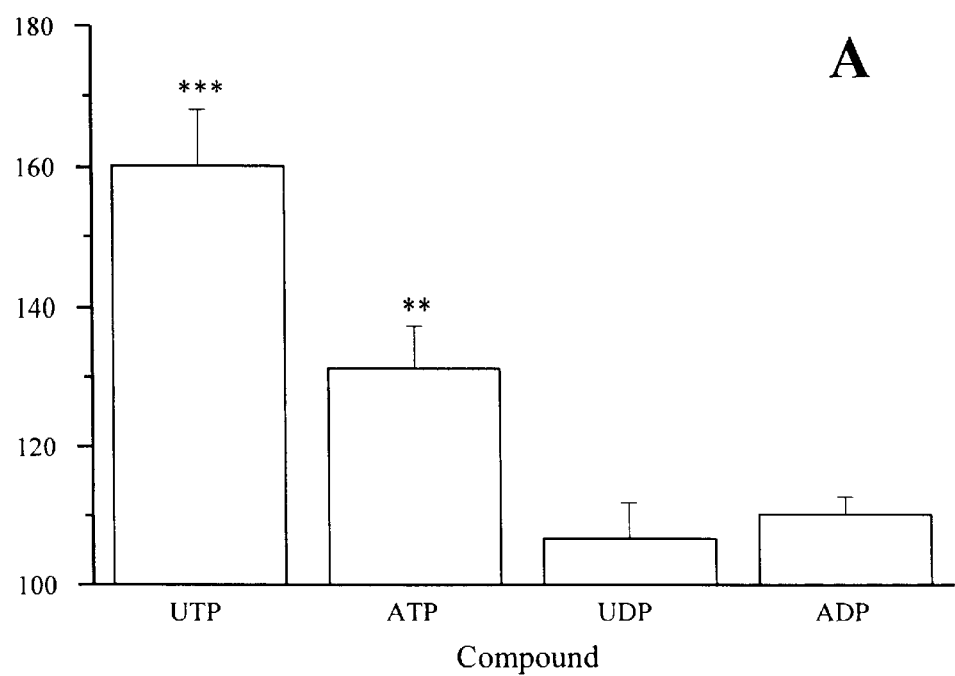
FIG. 3A shows the effects of ATP, UTP, ADP and UDP on tear secretion.
FIG. 3B shows the effect of $Ap_2A$, $Ap_3A$, $Ap_4A$, $Ap_5A$ and $Ap_6A$ on tear secretion.
Figure 3:
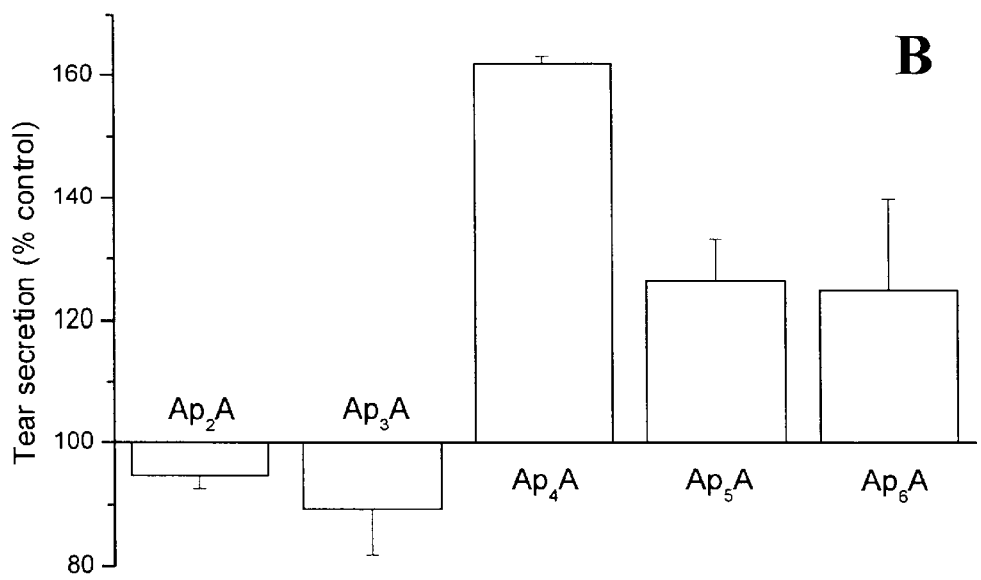

As shown in FIG. 3A, among the tested mononucleotides, UTP and ATP significantly increased Schirmer scores to 160±8% (n=16) (P<0.001) and 131±6%, respectively (n=12), when compared to control. UDP and ADP, on the other hand, did not significantly increase tear secretion, their values being 105±2% for UDP and 107±1% for ADP (n=10).

When diadenosine polyphosphates were assayed under the same conditions as the mononucleotides, $Ap_4A$, $Ap_5A$ and $Ap_6A$, significantly increased tear secretion, by 162±3%, 126±6% and 125±15%, respectively (p<0.05, n=12). Neither $Ap_2A$ nor $Ap_3A$ was able to significantly change tear secretion rates (95±2% and 89±7%, respectively, n=10) (FIG. 3B).

Figure 4:
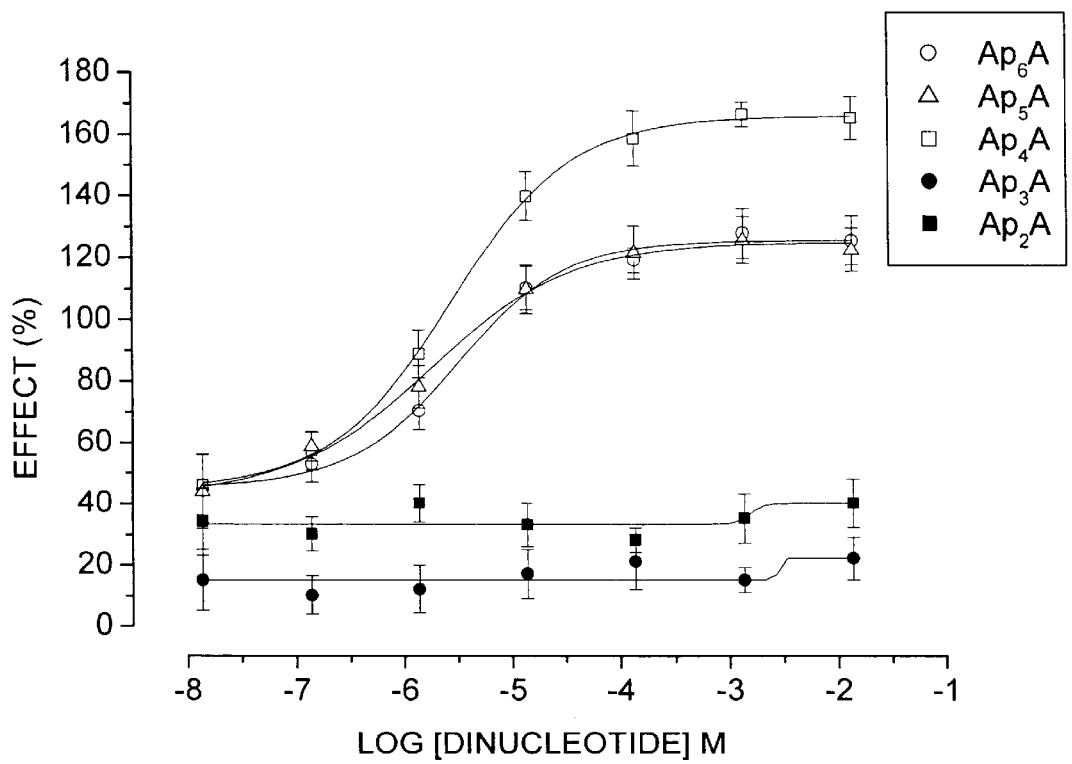
FIG. 4 shows the concentration-effect curves of dinucleotides $Ap_2A$, $Ap_3A$, $Ap_4A$, $Ap_5A$ and $Ap_6A$. Diadenosine polyphosphates, $Ap_2A$–$Ap_6A$ were assayed at concentrations ranging from $10^{-10}$ g/µl to $10^{-4}$ g/µl. Transormation of g/µl into M concentrations was performed by taking into account the corresponding molecular weight of each dinucleotide. Doses were applied in a non-cumulative fashion in one of the rabbit eyes, with the contralateral eye receiving the same volume of saline solution. Values are the mean ±S.E.M. of eight independent experiments.

Concentration-effect curves of all the dinucleotides in the range of $10^{-10}$ to $10^{-4}$ g/$\mu$l showed $pD_2$ values for $Ap_4A$, $Ap_5A$ and $Ap_6A$ of 5.56±0.03, 5.75±0.12 and 5.50±0.09 (n=8). These values corresponded to $EC_{50}$ values of 2.76 $\mu$M for $Ap_4A$, 1.77 for $Ap_5A$ and 3.16 $\mu$M for $Ap_6A$. $Ap_4A$ was the dinucleotide eliciting the strongest effect, 162±2.4%, with $Ap_5A$ and $Ap_6A$ exhibiting similar maximal effects (125±7%) (FIG. 4). Diadenosine diphosphate and diadenosine triphosphate failed to produce any change on tear secretion even at the highest concentrations assayed (n=8).

The lack of effect of UDP ($P2Y_6$ agonist) and ADP ($P2Y_1$ agonist), and moreover the full effect of $Ap_4A$, strongly suggested the involvement of a $P2Y_2$ receptor in this physiological action.

P2Y Receptor Results

Adenine dinucleotides were tested for their ability to activate human $P2Y_1$, $P2Y_2$, $P2Y_4$, $P2Y_6$ and $P2Y_{11}$ receptors as measured by the mobilization of intracellular $Ca^{2+}$. $P2Y_4$, $P2Y_6$ and $P2Y_{11}$ were insensitive to diadenosine polyphosphates and were only stimulated by different mononucleotides (results not shown).

Figure 5:
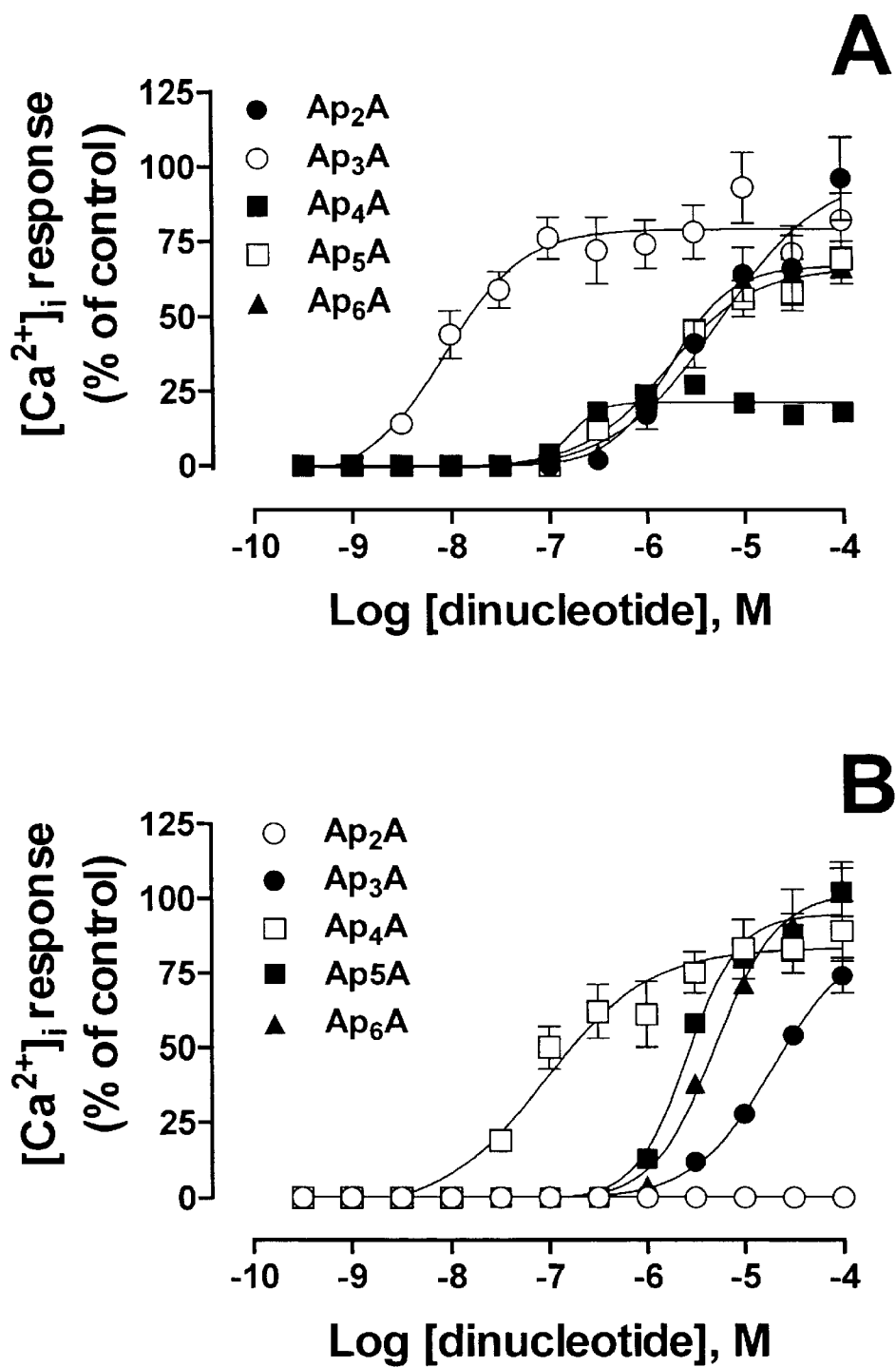
FIG. 5 shows the $[Ca^{+2}]_i$ responses to different concentrations of $Ap_2A$, $Ap_3A$, $Ap_4A$, $Ap_5A$ and $Ap_6A$: (A) $P2Y_1$ receptor, (B) $P2Y_2$ receptor.

Two receptors, $P2Y_1$ and $P2Y_2$, were fully activated by diadenosine polyphosphates with different pharmacological patterns (FIGS. 5A and B). The activity of $Ap_nA$ on human $P2Y_1$ and $P2Y_2$ receptors expressed in 01321 astrocytoma cells are shown in Table 2. The $P2Y_1$ receptor was fully activated by submicromolar concentrations of $Ap_3A$; the $P2Y_2$ receptor was activated by $Ap_4A$ at a similar low concentration.

TABLE 2

EC$_{50}$ and pD$_2$ values for intracellular calcium mobilization for Ap$_n$A on human P2Y$_1$ and P2Y$_2$ receptors expressed in 1321 astrocytoma cells (n = 3).
EC$_{50}$ ($\mu$M) (pD$_2$)

| Compound | P2Y$_1$ receptor | P2Y$_2$ receptor |
|---|---|---|
| Ap$_2$A | 5.67 (5.24) | N/A |
| Ap$_3$A | 0.009 (8.05) | 19.6 (4.70) |
| Ap$_4$A | 0.16 (6.77) | 0.093 (7.03) |
| Ap$_5$A | 1.66 (5.77) | 2.64 (5.57) |
| Ap$_6$A | 1.77 (5.75) | 5.18 (5.28) |

The invention and the manner and process of making and using it are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method of stimulating tear secretion and mucin production in eyes of a subject comprising the step of administering to the eyes of the subject an effective amount of a composition comprising a compound of Formula II or a pharmaceutically acceptable salt thereof:

FORMULA II

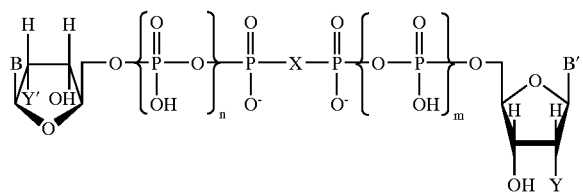

wherein:
X is oxygen, imido, methylene or difluoromethylene;
X is oxygen, imido, methylene or difluoromethylene;
Y is H or OH;
Y' is H or OH;
n=0, 1, or 2;
m=0, 1, or 2;
n+m=0–4; and
B and B' are each independently a purine residue, as in Formula IIa, linked through the 9-position:

FORMULA IIa

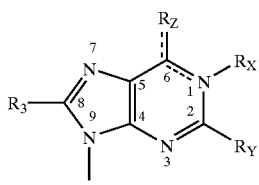

wherein:
R$_x$ is O, H or is absent;
R$_y$ is hydrogen, chlorine, amino, monosubstituted amino, disubstituted amino, alkylthio, arylthio, or aralkylthio, wherein the alkylthio, arylthio, or aralkylthio group contains up to a maximum of 20 carbon atoms, with or without unsaturation;

R$_z$ is oxo, mercapto, thione, alkylthio, arylthio, aralkylthio, acylthio, alkyloxy, aryloxy, aralkyloxy, acyloxy, amino, mono-substituted amino or di-substituted amino;

R$_3$ is hydrogen, azido, alkoxy, aryloxy, aralkyloxy, alkylthio, arylthio, aralkylthio, amino, mono-substituted amino, di-substituted amino, or T(C$_{1-6}$alkyl)OCONH(C$_{1-6}$alkyl)W wherein T and W are independently amino, mercapto, hydroxy or carboxyl, or pharmaceutically acceptable esters, amides or salts thereof.

2. The method according to claim 1, wherein said B and B' are adenine.

3. The method according to claim 2, wherein said n+m=2, 3, or 4, and said X=O.

4. The method according to claim 1, wherein said method is effective in treating dry eye disease.

5. The method according to claim 1, wherein said method is effective in treating corneal injury resulting from dry eye disease.

6. The method according to claim 1, wherein said administering is topical or systemic administering.

7. The method according to claim 6, wherein said topical administering of said composition is carried out via a carrier vehicle selected from a group consisting of drops of liquid, liquid wash, gels, ointments, sprays and liposomes.

8. The method according to claim 6, wherein said topical administering comprises infusing said composition to said ocular surface via a device selected from a group consisting of a pump-catheter system, a continuous or selective release device, and a contact lens.

9. The method according to claim 6, wherein said systemic administering is carried out via a liquid or liquid suspension via nose drops, nasal spray, or nebulized liquid, to oral or nasopharyngeal airways of said subject, such that a therapeutically effective amount of said compound contacts the lacrimal tissues of said subject via systemic absorption and circulation.

10. The method according to claim 6, wherein said systemic administering is carried out by administering an oral form, an injectable form, or a suppository form of said compound, such that a therapeutically effective amount of said compound contacts the lacrimal tissues of said subject via systemic absorption and circulation.

11. The method according to claim 6, wherein said systemic administering is carried out by administering an intra-operative instillation of a gel, cream, powder, foam, crystals, liposomes, spray or liquid suspension form of said compound, such that a therapeutically effective amount of said compound contacts the lacrimal tissues of said subject via systemic absorption and circulation.

12. The method according to claim 1, wherein said compound is administered in an amount sufficient to achieve concentrations thereof on the ocular surfaces of said subject of from about $10^{-7}$ to about $10^{-1}$ moles/liter.

13. A method of stimulating tear secretion and mucin production in eyes of a subject comprising the step of administering to the eyes of the subject an effective amount of a composition comprising P$^1$, P$^4$-di(adenosine-5'-)tetraphosphate, P$^1$, P$^5$-di(adenosine-5'-)pentaphosphate, P$^1$, P$^6$-di(adenosine-5'-)hexaphosphate, P$^1$, P$^4$-di(uridine-5'-)tetraphosphate, P$^1$-(deoxycytidine 5'-) P$^4$-(uridine 5'-)tetraphosphate, P$^1$-(bromophenylethenocytidine 5'-) P$^4$-(uridine 5'-) tetraphosphate, or P$^1$-(inosine 5'-) P$^4$-(uridine 5'-) tetraphosphate, or a pharmaceutically acceptable salt thereof.

14. A method of treating dry eye disease of a subject comprising the step of administering to the eyes of the subject an effective amount of a composition comprising P$^1$, P⁴-di(adenosine-5'-)tetraphosphate, P¹, P⁵-di(adenosine-5'-)pentaphosphate, P¹, P⁶-di(adenosine-5'-)hexaphosphate, P¹, P⁴-di(uridine-5'-)tetraphosphate, P¹-(deoxycytidine 5'-) P⁴-(uridine 5'-) tetraphosphate, P¹-(bromophenylethenocytidine 5'-) P⁴-(uridine 5'-) tetraphosphate, or P¹-(inosine 5'-) P⁴-(uridine 5'-) tetraphosphate, or a pharmaceutically acceptable salt thereof.

15. A method of treating corneal injury of a subject com-comprising the step of administering to the eyes of the subject an effective amount of a composition comprising P¹, P⁴-di(adenosine-5'-)tetraphosphate, P¹, P⁵-di(adenosine-5'-)pentaphosphate, P¹, P⁶-di(adenosine-5'-)hexaphosphate, P¹, P⁴-di(uridine-5'-)tetraphosphate, P¹-(deoxycytidine 5'-) P⁴-(uridine 5'-) tetraphosphate, P¹-(bromophenylethenocytidine5'-) P⁴-(uridine 5'-) tetraphosphate, or P¹-(inosine 5'-) P⁴-(uridine 5'-) tetraphosphate, or a pharmaceutically acceptable salt thereof, wherein said corneal injury results from dry eye disease.

16. A method of stimulating tear secretion and mucin production in eyes of a subject comprising the step of administering to the eyes of the subject an effective amount of a composition comprising a compound of Formula II or a pharmaceutically acceptable salt thereof:

FORMULA II

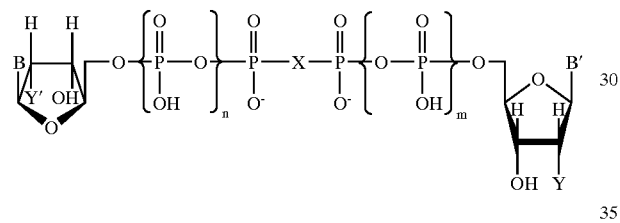

wherein:
X is oxygen, imido, methylene or difluoromethylene;
Y is H, or OH;
Y' is H, or OH;
n=0, 1, or 2;
m=0, 1, or 2;
n+m=0–4; and
B is a purine residue, as in Formula IIa, B' is a pyrimidine residue, as in Formula IIb, B and B' are linked through the 9- or 1-position, respectively;

FORMULA IIa

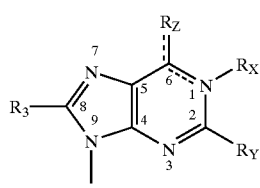

wherein:
$R_x$ is O, H or is absent;
$R_y$ is hydrogen, chlorine, amino, monosubstituted amino, disubstituted amino, alkylthio, arylthio, or aralkylthio, wherein the alkylthio, arylthio, or aralkylthio group contains up to a maximum of 20 carbon atoms, with or without unsaturation;
$R_z$ is oxo, mercapto, thione, alkylthio, arylthio, aralkylthio, acylthio, alkyloxy, aryloxy, aralkyloxy, acyloxy, amino, mono-substituted amino or di-substituted amino;
$R_3$ is hydrogen, azido, alkoxy, aryloxy, aralkyloxy, alkylthio, arylthio, aralkylthio, amino, mono-substituted amino, di-substituted amino, or $T(C_{1-6}alkyl)OCONH(C_{1-6}alkyl)W$ wherein T and W are independently amino, mercapto, hydroxy or carboxyl, or pharmaceutically acceptable esters, amides or salts thereof;

Formula IIb

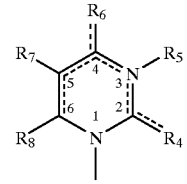

wherein:
$R_4$ is hydroxy, oxo, mercapto, thione, amino, cyano, $C_{7-12}$arylalkoxy, $C_{1-6}$ alkylthio, $C_{1-6}$ alkoxy, $C_{1-6}$ alkylamino or di$C_{1-4}$alkylamino, wherein the alkyl groups are optionally linked to form a heterocycle;
$R_5$ is hydrogen, acetyl, benzoyl, $C_{1-6}$ alkyl, $C_{1-5}$ alkanoyl, aroyl, or absent;
$R_6$ is hydroxy, oxo, mercapto, thione, $C_{1-4}$alkoxy, $C_{7-12}$arylalkoxy, $C_{1-6}$alkylthio, S-phenyl, arylthio, arylalkylthio, triazolyl amino, $C_{1-6}$alkylamino, $C_{1-5}$ disubstituted amino, or di-$C_{1-4}$alkylamino, wherein said dialkyl groups are optionally linked to form a heterocycle or linked to form a substituted ring such as morpholino, pyrrolo; or
$R_5$ and $R_6$ taken together form a 5-membered fused imidazole ring of 3,$N^4$-ethenocytosine derivatives between positions 3 and 4 of the pyrimidine ring, wherein said etheno moiety is optionally substituted on the 4- or 5-positions with $C_{1-4}$ alkyl, phenyl or phenyloxy; wherein at least one hydrogen of said $C_{1-4}$ alkyl, phenyl or phenyloxy is optionally substituted with a moiety selected from the group consisting of halogen, hydroxy, $C_{1-4}$ alkoxy, $C_{1-4}$ alkyl, $C_{6-10}$ aryl, $C_{7-12}$ arylalkyl, carboxy, cyano, nitro, sulfonamido, sulfonate, phosphate, sulfonic acid, amino, $C_{1-4}$ alkylamino, or di- $C_{1-4}$ alkylamino, wherein said dialkyl groups are optionally linked to form a heterocycle;
$R_7$ is hydrogen, hydroxy, cyano, nitro, $C_{1-6}$ alkyl or phenyl, substituted $C_{2-8}$ alkynyl, halogen, substituted $C_{1-4}$ alkyl, $CF_3$, $C_{2-3}$ alkenyl, $C_{2-3}$ alkynyl, allylamino, bromovinyl, ethyl propenoate, propenoic acid or $C_{2-8}$ alkenyl; or
$R_6$ and $R_7$ together form a 5 or 6-membered saturated or unsaturated ring bonded through N or O or S at $R_6$, such ring optionally contains substituents that themselves contain functionalities;
$R_8$ is hydrogen, amino, di-$C_{1-4}$alkylamino, $C_{1-4}$alkoxy, $C_{7-12}$arylalkoxy, $C_{1-4}$alkylthio, $C_{7-12}$ arylalkylthio, carboxamidomethyl, carboxymethyl, methoxy, methylthio, phenoxy, or phenylthio; provided that when $R_8$ is amino or substituted amino, $R_7$ is hydrogen.

17. The method according to claim 16, wherein said method is effective in treating dry eye disease.

18. The method according to claim 16, wherein said method is effective in treating corneal injury resulting from dry eye disease.

* * * * *